(12) United States Patent
Faller et al.

(10) Patent No.: US 6,611,709 B2
(45) Date of Patent: Aug. 26, 2003

(54) STORAGE OF DEFIBRILLATION ELECTRODES (75) Inventors: Frederick W. Faller, Burlington, MA (US); Ward Hamilton, Amherst, NH (US); Michael R. Dupelle, N. Attleboro, MA (US); Wayne A. Reval, Haverhill, MA (US)

(73) Assignee: ZMD Corporation, Wilmington, DE (US)

( * ) Notice: Subject to any disclaimer, the term of this patent is extended or adjusted under 35 U.S.C. 154(b) by 0 days.

(21) Appl. No.: 09/967,492

(22) Filed: Sep. 28, 2001

(65) Prior Publication Data

US 2003/0065363 A1 Apr. 3, 2003

(51) Int. Cl.⁷ ................................................. A61N 1/39
(52) U.S. Cl. ............................. 607/5; 607/36; 206/438
(58) Field of Search ............................ 206/210, 363, 206/370, 438, 557–565, 569–571, 701–707; 600/372, 382, 386, 391–393; 607/1–2, 4–5, 36, 115, 142, 148, 149, 152, 153

(56) References Cited

U.S. PATENT DOCUMENTS

| 5,415,282 A | * | 5/1995 | Kienholz ..................... 206/216 |
| 6,041,255 A | * | 3/2000 | Kroll .............................. 607/5 |
| 6,397,104 B1 | * | 5/2002 | Miller et al. ................... 607/5 |
| 2002/0082644 A1 | * | 6/2002 | Picardo et al. ................. 607/1 |

OTHER PUBLICATIONS

U.S. application Ser. No. 09/938,021, filed Aug. 23, 2001.
* cited by examiner Primary Examiner—Kennedy Schaetzle
Assistant Examiner—Kristen Droesch
(74) Attorney, Agent, or Firm—Fish & Richardson P.C.

(57) ABSTRACT

A defibrillator in which electrodes with a limited shelf life are stored largely out of view from the exterior of the unit, but the expiration date or other marking indicative of expiration or failure is positioned so as to be visible from the exterior of the defibrillation unit. A fracturable member is attached to the defibrillation unit so that opening the defibrillation unit requires fracturing the member, thereby providing an indication of whether the unit has been opened. Electrodes are releasably attached to the inside of the cover of a defibrillator, so that when the cover is removed the electrodes remain with the cover.

22 Claims, 6 Drawing Sheets

STORAGE OF DEFIBRILLATION ELECTRODES

CROSS-REFERENCE TO OTHER APPLICATIONS

This application incorporates by reference the disclosure of U.S. patent application Ser. No. 09/938,021, filed Aug. 23, 2001, entitled "Defibrillators".

BACKGROUND

Public access defibrillators (PADs) are designed to be used by lay caregivers and/or emergency workers such as EMTs and firefighters to resuscitate victims of cardiac arrest. PADs are likely to be stored in public places, where they can be readily located and used by these caregivers and emergency workers. They may hang on walls, be stored on shelves, or even in the trunks of vehicles.

Each PAD typically includes a defibrillator unit and a pair of disposable electrodes. The pair of electrodes is stored inside an electrode package or pouch (or each electrode within a separate package). The electrodes must be removed from the package, applied to the victim's chest, and the electrode cables connected to the defibrillator unit. EKG signals detected through the electrodes are analyzed by electronics within the defibrillator unit, to determine the cardiac condition of the victim. If defibrillation is required a defibrillation pulse is delivered through the same electrodes.

Depending on the design of the PAD, the electrode package may be stored inside the defibrillation unit, e.g., inside a cover plate, to protect it from damage that might occur if it were exposed.

The electrodes have a limited shelf life, and must be periodically replaced. For example, electrodes containing an aqueous gel will eventually dry out or corrode the metallic elements of the electrode. As a typical PAD will not often be used—indeed, it can be expected that most PADs will never be used—it cannot be assumed that electrodes will be used, and thus replaced, prior to expiration of their shelf life. Instead it is typical for PADs to be periodically inspected to be sure that their electrodes have not expired. This is typically done by reading the expiration date from a label on the exterior of the electrode package.

SUMMARY

In a first aspect, the invention features a defibrillator in which electrodes with a limited shelf life are stored largely out of view from the exterior of the unit, but the expiration date or other marking indicative of expiration or failure is positioned so as to be visible from the exterior of the defibrillation unit.

In preferred implementations, one or more of the following features may be incorporated. The defibrillation unit may have an opening through which a tab connected to the electrodes extends, with the expiration date or other marking positioned so as to be on the visible portion of the tab. The electrodes may be contained within one or two electrode packages, and a tab may extend from one or both of the packages. A single package may contain both electrodes, and a tab may extend from the single package. The defibrillation unit may include a cover and a base unit to which the cover is attached, the electrodes may be stored between the cover and the base unit, and the expiration date or other marking may be positioned on a tab extending from the electrodes to the exterior of the defibrillation unit.

In a second aspect, the invention features a fracturable member attached to the defibrillation unit so that opening the defibrillation unit requires fracturing the member, thereby providing an indication of whether the unit has been opened.

In preferred implementations, one or more of the following features may be incorporated. The fracturable member may have a visible portion carrying the expiration date or other marking indicative of electrode failure or expiration. The defibrillation unit may have a cover and a base unit to which the cover is attached, and opening the cover will fracture the member. The fracturable member may be an elongated band, and the band may be adhesively attached to at least one portion of the defibrillation unit. The band and adhesive attachment may be configured so that the band will fracture if an effort is made to detach the band at a location at which it is adhesively attached to the defibrillation unit. The fracturable member may be configured to tear if the defibrillation unit is opened.

In a third aspect, the invention features a defibrillator in which electrodes are stored between a cover and a base unit of the defibrillator, and in which the electrodes are releasably attached to the inside of the cover, so that when the cover is removed from the base unit the electrodes remain with the cover.

In preferred implementations, one or more of the following features may be incorporated. The electrodes may be contained within at least one package, and the releasable attachment of the electrodes to the inside of the cover may be provided by releasable attachment of the package to the inside of the cover. At least one tab member may extend from the electrode package, and the tab member may be releasably attached to the inside of the cover. The tab or elongated band on which expiration or other marking is carried may also serve as the releasable connection of the electrode package to the cover. The tab may extend through an opening in the cover, and may have tapered wings that require less force to insert into the opening in the cover than to remove from the opening.

In its various aspects, and preferred embodiments, the invention has numerous advantages (not all of which are present in all aspects and embodiments). Users are able to readily ascertain whether the electrodes have expired, and whether the defibrillator has been tampered with. This reduces the time required for routine inspection of the defibrillator. Because inspection for electrode expiration can be done without opening the cover of the defibrillator, and without handling the electrode package, the likelihood of premature electrode failure from repeated handling is greatly reduced. It can be readily ascertained whether the defibrillator has been opened or tampered with. The electrode package is conveniently held adjacent the inside of the cover as it is removed, so that it does not obscure the controls of the unit.

Other features of the invention will be apparent from the following detailed description, including the drawings, and from the claims.

DETAILED DESCRIPTION

Figure 1:
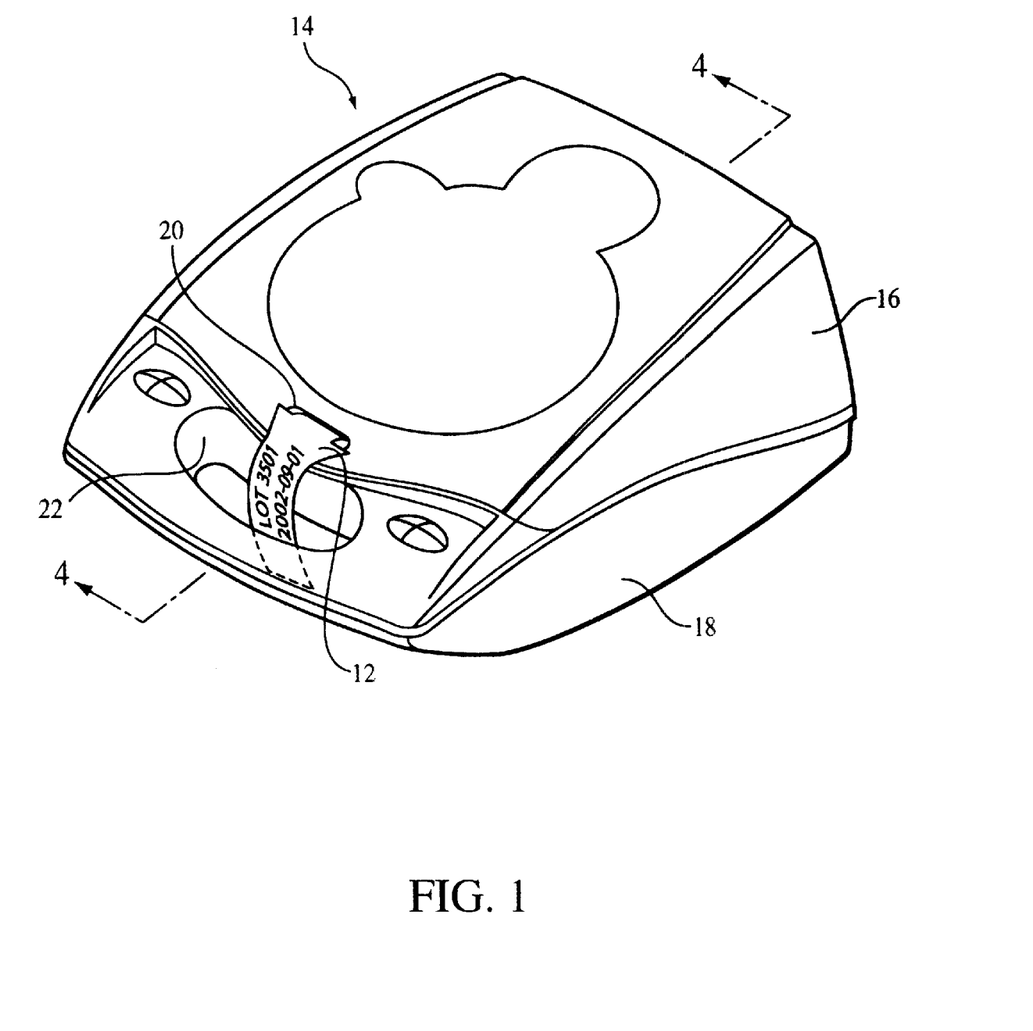
FIG. 1 is a perspective view of the exterior of a defibrillation unit, showing the anti-tampering, expiration-indicating tab of a preferred embodiment of the invention.
Figure 2:
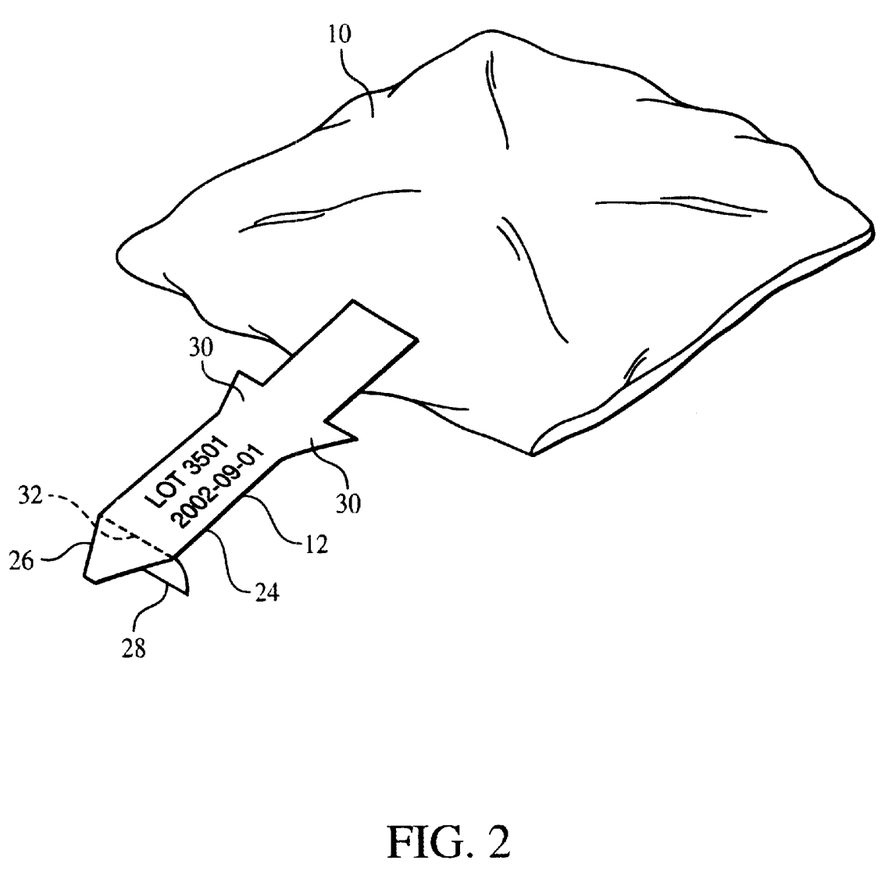
FIG. 2 is a perspective view of the electrode package of a preferred embodiment of the invention, prior to insertion of the electrode package into the defibrillation unit.
Figure 3:
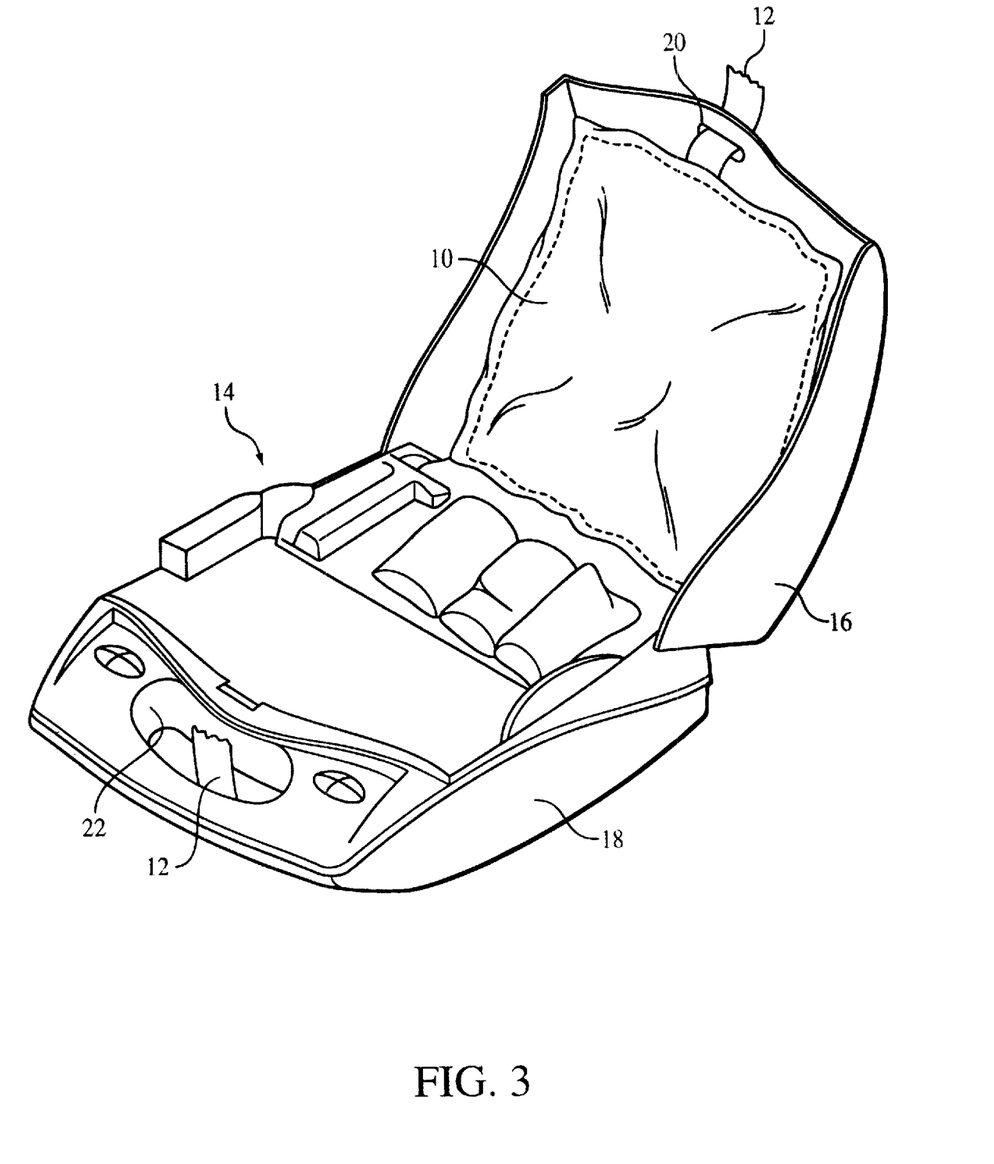
FIG. 3 is a perspective view of the electrode package of FIG. 2 held inside the opened cover of the defibrillation unit of FIG. 1.
Figure 4:
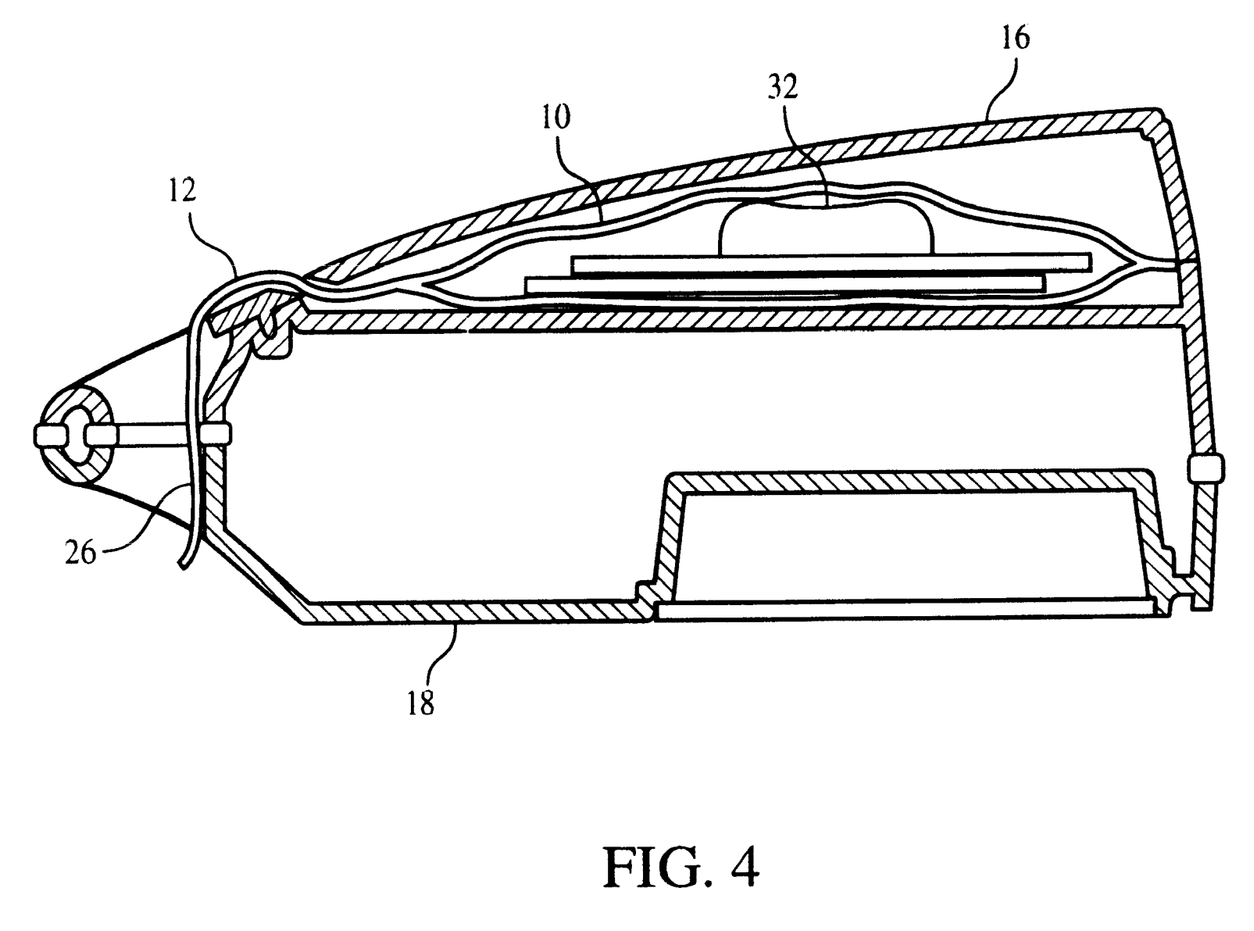
FIG. 4 is a cross-sectional view taken at 4—4 in FIG. 1.
Figure 5:
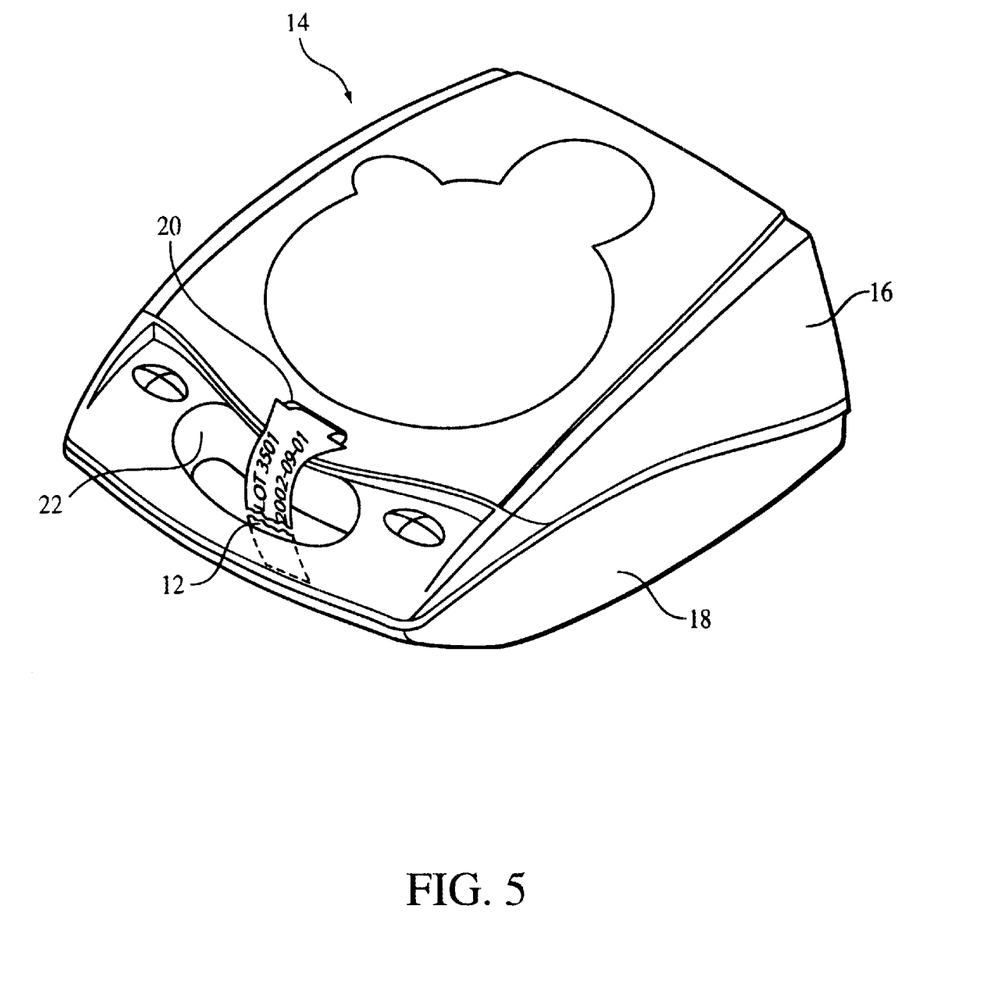
FIG. 5 is a perspective view similar to FIG. 1, but showing the anti-tampering, expiration-indicating tab torn as the result of the cover having been disturbed.

As shown in FIGS. 1 and 2, the electrode package 10 (which contains a pair of electrodes) includes an anti-tampering, expiration-indicating tab 12 that is preferably permanently fastened to the electrode package 10, and so positioned that when the electrode package is placed in the defibrillation unit 14 the tab extends from the unit through a slot 20 in the cover 16 of the unit. The tab is fed down through the opening 22 forming the handle of the unit, and fastened at its end region 26 with adhesive to the base 18 of the unit. A release liner 28 is removed from the backside of the tab to expose the adhesive. End region 26 is preferably tapered to ease insertion of the tab through slot 20 in the cover (but many other shapes could be used). The tab shown is about 4.75 inches in length and 1.0 inches wide, and constructed from paper laminated between two layers of plastic (UPVC or polyester), with an overall thickness of about 0.010 inches. It is adhered to the electrode package 10 by a permanent pressure sensitive acrylic adhesive (40 oz tear strength on steel per ASTM D-3330) over about a 1.0 inch overlap with the package. The package material is a laminate of polyester, aluminum, and Surlyn with an MVTR of less than about 0.020 inches. End region 26 occupies approximately the final 0.5 inches of the tab, and consists only of paper. The plastic laminated layers end about 0.5 inches short of the end of the tab. The paper is adhered to the base unit with a layer of adhesive (tear strength 30 oz. on steel per ASTM D-3330). The adhesive coating is protected by a release liner that is removed to adhere the end region to the base. The laminated portion of the tab, which is not intended to be torn, has a tear strength of about 40 lb (per ASTM D-3759). It is expected that the end region 26 will tear away from the tab along a tear line 32 located about 0.5 inches from the end of the tab, at approximately the boundary between the plastic/paper laminated portion of the tab and the all-paper end region 26.

Fastened as described, the tab forms a seal (FIG. 1), preventing a user or an inquisitor from opening the cover of the unit without breaking the seal. Since the expiration date and lot code (e.g., "Jan. 9, 2002, Lot 3501"), or other pertinent information about the electrodes, is printed on the tab, there is no reason for someone to open the cover except to use the device or to replace the electrodes on expiration. When the cover is opened, the end region 26 separates from the tab along a tear line 32, leaving the portion of the tab bearing the expiration date and lot code still adhered to the electrode package. This "permanent" connection of the tab to the electrode package is preferred, as it means that the electrode package, even after the electrodes have been used, can be examined to ascertain the important lot code and expiration date information. Such information could be invaluable in researching the cause of an electrode failure during defibrillation.

End portion 26 is also designed to expose any effort to peel off the tab and reapply it to cover up the fact of the unit being tampered with. The adhesive used to bond the paper to the base has a high tear strength, and the paper is relatively fragile, with the result that it is very difficult, if not impossible, to remove the paper without visibly damaging it.

The tab may also serve an entirely different function, of supporting the electrode package within the inside of the cover so that when the cover is removed the electrode package stays adjacent the inside of the cover. This is achieved by forming arrow-shaped wings 30 on the tab. The wings extend about 0.25 to 0.50 inches from the edge of the tab, and are spaced about 0.25 inches from the edge of the pouch. The wings can easily be pulled through slot 20 to install the electrode package inside the cover, but when the seal is broken and the cover is lifted, the shoulders help retain the electrode package on the inside surface of the cover, thereby pulling the package free of the control panel (or "interface"), which is exposed on the top of the base 18 when the cover is removed. The wings 30 are preferably made of the same flexible plastic/paper laminated material as the body of the tab. They are strong enough to cause the electrode package to stay adjacent the inside of the cover when the cover is removed, but they are also flexible enough that they can easily be overpowered to remove the electrode package from the cover.

Other embodiments of the invention are within the following claims.

Some examples follow; many others are possible.

While it is preferred that the tab be "permanently" connected to the electrode package—meaning that the tab is very likely to stay attached during normal use and be there for examination after defibrillation—the tab could be a separable member removed from the electrode package and connected to the base and cover, e.g., in a location comparable to that shown in the figures (but not extending into the cover through a slot).

In embodiments in which there is a tab extending from the electrode package, the tab could be connected to the electrode package in various ways other than with adhesive. E.g., snaps, rivets, or heat sealing could be used. Or a unitary extension of the material making up the electrode package could provide the tab.

Other techniques than a tab extending from the unit could be employed to expose the expiration date and other information printed on the electrode package. A window could be provided in the cover, through which the information can be read from the package. The cover could be shaped so as to expose a portion of the electrode package (e.g., a corner or one edge) on which the information appears.

Instead of using an all paper end portion, the tab could be constructed entirely of a plastic material, or a laminate of plastic and paper, with perforations designed to tear upon any effort to open the cover.

The location of the tear line could be moved from what is disclosed in the detailed description and drawings. E.g., it could be more centrally located on the tab.

A tab of very different shape could be used in place of the rectangular one shown in the drawings. The tab could, for example, be a curved bulge in the edge of the electrode package. The tab could be replaced by a filament like member (e.g., a length of breakable string) secured to the cover and base.

Instead of adhering the end of the tab to the base unit with adhesive, the end could be connected in many other ways, e.g., a snap member, clamp, gripping member, or other mechanical fastening technique could be used. Any of several techniques in which a tool is used to fasten the tab to the base unit could also be used, with the fastening being done so that it cannot be taken apart without access to the same tool, which would not be readily available to the public. Another mechanical fastening technique would be to use an enlarged arrow-shaped tip on the tab, with the dimensions of the tip and a slot in the base into which it is inserted so sized and configured that the tip would be irreversibly captured in the base upon insertion into the slot. Thus, once inserted, the tab could not be removed without its being torn.

The tab need not extend through a slot in the cover, or into a handle opening on the base of the unit. These are just one of many ways of arranging for the tab to seal between the cover and the base unit.

The electrodes could be stored in other locations than on the inside surface of the cover. E.g., they could be on a shelf below the base unit. A tab could extend from there up and onto the cover.

Other techniques than wings 30 on the tab could be used to support the electrode package so that it tends to stay adjacent the inside of the cover. E.g., releasable adhesive could be used to secure the electrode package to the inside surface of the cover.

The defibrillation electrodes could be two separate electrodes each connected to the defibrillator by a cable, or the two electrodes could be installed on a single substrate. Typically, both electrodes, whether separate or on one substrate, could be contained within a single electrode package. But if the electrodes are separate they could be contained in separate electrode packages. In which case each package could have a portion bearing expiration date or other information visible from the exterior of the defibrillation unit. Alternatively, the packages could each have a tab similar to the one tab disclosed above, with two tabs extending to the exterior of the defibrillation unit and sealing the cover to the base. Still another alternative would be to have one package bonded, e.g., by adhesive, to the other package, and have only one tab extend to the exterior.

Electrodes are usually stored in packages, and these packages are what would be stored within the defibrillation unit, the invention could be practiced even if the electrodes were stored without packaging.

The expiration date or other marking that the invention makes visible on the exterior of the defibrillation unit could simply be printed characters, but it could also be in a form that can be scanned by a bar code or other type of scanner. And the content could include a variety of information indicative of the expiration or failure of the electrodes, including, e.g., date of expiration, date of manufacturing, manufacturer identity, lot number.

Most importantly, it needs to be understood that different aspects of the invention can be practiced independently of other aspects. For example, configuring the electrode package and defibrillation unit so that the expiration date or other marking on the electrode package can be viewed from the exterior can be practiced without the use of an anti-tampering, tearable member attached between the cover and the base unit. And the converse is true, as the anti-tampering member could be used without any expiration date or other information about the electrode being provided. And that aspect of the invention having to do with supporting the electrode package adjacent the inside surface of the cover could be practiced with or without the other aspects, as it is independent of the concepts of an anti-tampering seal and positioning an electrode expiration date (or other information) marking so that it can be read from the exterior.

Figure 6:
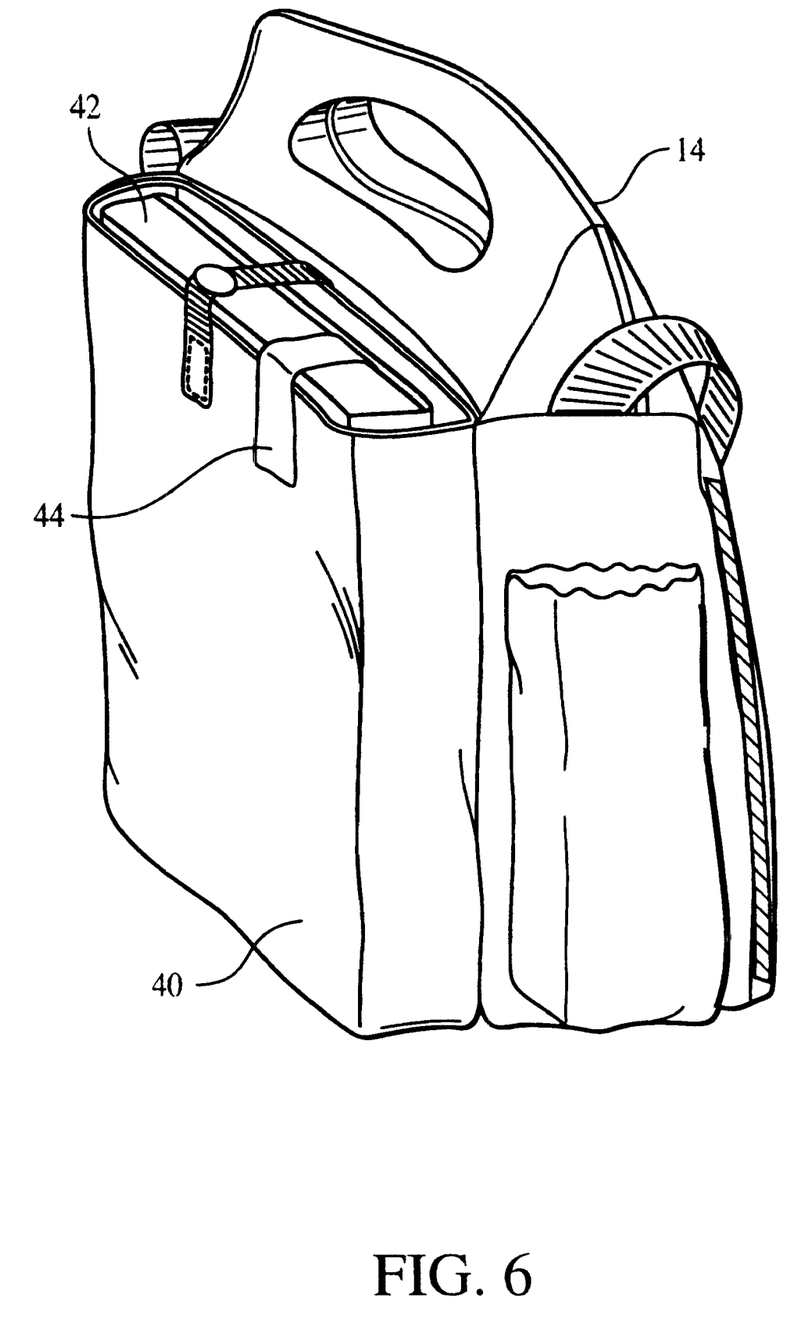
FIG. 6 is a perspective view of a carrying case in which a defibrillation unit and a spare box of electrodes is stored.

Finally, at least two of the aspects of the invention could be applied to carrying cases in which defibrillation electrodes are stored. One example of such a case is shown in FIG. 6. It is very common for defibrillators used by EMTs to be stored in a carrying case 40 along with related gear, including a box 42 of spare electrodes. The aspect of the invention in which the expiration date or other information is made visible from the exterior of a container without opening could be usefully applied to these pockets or compartments of the carrying cases, as that would save the user from having to routinely inspect the status of electrodes in the pockets or compartments. The anti-tampering seal aspect of the invention could also be applied, by providing such a seal across the opening of the pocket or compartment. Tab 44 could extend from the electrode package, to the exterior of the box 42, and then be attached to the carrying case in such a manner that removal of the box would require tearing the tab. The manner of attachment to the carrying case is not shown in FIG. 6, but could be done with a special tool not readily available. That way in the field the tab would have to be torn to remove the box, but the special tool could later be used when inserting a new box and removing the stub of the old tab.

What is claimed is:

1. A defibrillator, comprising:

a defibrillation unit capable of delivering a defibrillation pulse;

one or more defibrillation electrodes for delivering the defibrillation pulse; and packaging associated with the electrodes;

wherein the electrodes hay a limited shelf life and wherein an expiration date or other marking indicative of expiration or failure of the electrodes is marked on the electrodes or packaging;

wherein the electrodes and packaging are stored within the defibrillation unit primarily out of view from the exterior of the defibrillation unit; and wherein the expiration date or other marking is positioned so as to be visible from the exterior of the defibrillation unit.

2. The defibrillator of claim 1 wherein the defibrillation unit has an opening, and the electrodes or packaging associated with the electrodes comprise a tab with a visible portion extending through the opening, and wherein the expiration date or other marking is positioned so as to be on the visible portion of the tab.

3. The defibrillator of claim 2 wherein the electrodes are contained within one or two electrode packages, and the tab extends from at least one of the electrode packages.

4. The defibrillator of claim 3 wherein a single package contains both electrodes, and the tab extends from the single package.

5. The defibrillator of claim 1 wherein the defibrillation unit comprises a cover and a base unit to which the cover is attached;

wherein the electrodes are stored between the cover and the base unit, wherein the expiration date r other marking is positioned on a tab extending from the electrodes or packaging associated with the electrodes to the exterior of the defibrillation unit.

6. The defibrillation unit of claim 1 wherein the expiration date r other marking is positioned on a member extending from the electrodes or packaging associated with the electrodes to the exterior of the defibrillation unit, wherein the member is configured to fracture if the defibrillation unit is opened, thereby providing an indication of whether he unit has been opened.

7. A defibrillator, comprising:
a defibrillation unit capable of delivering a defibrillation pulse, wherein the defibrillation unit comprises a cover and a base it to which the cover is attached;
one or more defibrillation electrodes for delivering the defibrillation pulse;
packaging surrounding the electrodes;
wherein the electrodes and packaging in are stored within the interior of the defibrillation unit between the cover and the base unit, primarily out of view from the exterior of the unit; and
a fracturable member attached to the defibrillation unit so that opening the defibrillation unit by removing the cover from the unit requires fracturing the member, and thereby providing an indication of whether the unit has been opened.

8. The defibrillator of claim 6
wherein the defibrillation unit comprises a cover and a base unit to which the cover is attached;
wherein the electrodes are stored between the cover and the base unit, primarily out of view from the exterior of the unit; and
wherein opening the defibrillation unit comprises removing the cover from the unit.

9. The of claim 6 or 7 wherein the fracturable member is an defibrillator elongated band.

10. The defibrillator of claim 9 wherein the elongated band is adhesively attached to at least one portion of the defibrillation unit.

11. The defibrillator of claim 10 wherein the elongated band and adhesive attachment are configured so that the band will fracture if an effort is made to detach the band at a location at which it is adhesively attached to the defibrillation unit.

12. The defibrillator of claim 9 wherein the elongated band extends through an opening in the cover, and the elongated band comprises tapered wings extending from its sides to engage the cover.

13. The defibrillator of claim 6 or 7 wherein the fracturable member is configured to tear if the defibrillation unit is opened.

14. A defibrillator, comprising:
a defibrillation unit capable of delivering a defibrillation pulse;
one or more defibrillation electrodes for delivering the defibrillation pulse;
packaging surrounding the electrodes
wherein the defibrillation unit comprises a cover and a base unit to which the cover is attached;
wherein the electrodes and packaging in are stored between the cover and the base unit; and
wherein the electrodes and packaging in are releasably attached to an inside surface of the cover, so that when the cover is removed from the base unit the electrodes and packaging remain with the cover.

15. The defibrillator of claim 14 wherein the electrodes are contained within at least one package, and the releasable attachment of the electrodes to the inside of the cover is provided by releasable attachment f the package to the inside of the cover.

16. The defibrillator of claim 15 further comprising at least one tab member extending from the electrode package, wherein the tab member is releasably attached to the inside of the cover.

17. The defibrillator of claim 16 wherein the tab member bears an expiration date associated with the electrodes or other marking indicative of the expiration date or failure of the electrodes, and wherein that portion of the tab member bearing the expiration date or other marking extends through an opening in the cover.

18. The defibrillator of claim 17 wherein the tab comprises tapered wings that require less force to insert into the opening in the cover than to remove from the opening.

19. A defibrillator carrying case in which a defibrillation electrode package has been stored in a pock t or compartment, comprising:
a space for receiving a reusable defibrillator;
an electrode package pock t or compartment in the carrying case;
a defibrillator electrode package stored within the pocket or compartment wherein the electrode has a limited shelf life, and wherein an expiration date or other marking indicative of expiration or failure f the electrode is marked on the electrode package;
wherein the electrode package comprises a tab on which is marked the expiration date or other marking;
wherein the pocket or compartment has an opening through which the tab extends sufficiently that the expiration date or other marking is visible from outside the pocket or compartment.

20. The carrying case of claim 19 wherein the tab is a fracturable member that is attached in the vicinity of the opening of the pocket or compartment so that opening the pocket or compartment requires fracturing the member, and thereby providing an indication of whether the pocket or compartment has beet opened.

21. A reusable carrying case for a reusable defibrillator in which a defibrillation electrode package has been stored in a pocket or compartment, comprising
a space for receiving a reusable defibrillator;
an electrode package pocket or compartment in the carrying case;
a defibrillator electrode package stored within the pocket or compartment;
a fracturable member attached in the vicinity of an opening of the pocket or compartment so that opening the pocket or compartment requires fracturing the member, and thereby providing an indication of whether the pocket or compartment has been opened.

22. The carrying case of claim 21 wherein the fracturable member is an elongated band that is connected so that the band must be torn to gain access to the pocket or compartment.

* * * * *

UNITED STATES PATENT AND TRADEMARK OFFICE
CERTIFICATE OF CORRECTION

PATENT NO. : 6,611,709 B2
DATED : August 26, 2003
INVENTOR(S) : Frederick W. Faller et al.

It is certified that error appears in the above-identified patent and that said Letters Patent is hereby corrected as shown below:

Column 3,
Line 48, "Jan. 9, 2002" should be -- 2002-09-01 --.

Column 6,
Line 28, "hay" should be -- have --.
Lines 56 and 61, "r" should be -- or --.
Line 67, "he" should be -- the --.

Column 7,
Line 4, "it" should be -- unit --.
Lines 8, 53 and 55, after "packaging", delete "in".
Lines 26 and 27, after "The", insert -- defibrillator --, and after "an", delete "defibrillator".
Line 49, after "electrodes", insert -- ; --.

Column 8,
Line 2, "f" should be -- of --.
Lines 18 and 21, "pock t" should be -- pocket --.
Line 26, "f" should be -- of --.
Line 40, "beet" should be -- been --.

Signed and Sealed this

Thirteenth Day of April, 2004

JON W. DUDAS
*Acting Director of the United States Patent and Trademark Office*